United States Patent [19]

Carman

[11] Patent Number: 5,411,548
[45] Date of Patent: * May 2, 1995

[54] METHOD OF VARYING APPROPRIATE MUSCLE STRENGTH OF A PERSON TO ALLEVIATE URINARY OR FECAL URGENCY OR INCONTINENCE OR VAGINAL OR BLADDER SPASMS

[76] Inventor: Brent Carman, R.R. #1, Millarville, Alberta, Canada

[*] Notice: The portion of the term of this patent subsequent to Mar. 8, 2011 has been disclaimed.

[21] Appl. No.: 172,301

[22] Filed: Dec. 23, 1993

Related U.S. Application Data

[63] Continuation-in-part of Ser. No. 3,052, Jan. 11, 1993, Pat. No. 5,291,902.

[51] Int. Cl.$^6$ .............................................. A61N 1/00
[52] U.S. Cl. ...................................... 607/138; 128/733
[58] Field of Search ............... 128/733, 734, 774, 775, 128/778, 782; 607/138

[56] References Cited

U.S. PATENT DOCUMENTS

| | | | |
|---|---|---|---|
| 4,170,225 | 10/1979 | Criglar et al. | 128/733 |
| 4,396,019 | 8/1983 | Perry | 128/733 |
| 5,259,388 | 11/1993 | Eisman et al. | 128/733 |
| 5,291,902 | 3/1994 | Carman | 607/138 |

*Primary Examiner*—Max Hindenburg
*Attorney, Agent, or Firm*—Rogers & Scott

[57] ABSTRACT

A method of varying the appropriate muscle strength of a person to at least alleviate urinary or fecal urgency or incontinence, or vaginal or bladder spasms, includes placing a surface electrode of electromyographic measuring apparatus at an appropriate position on the person and/or inserting a probe electrode of electromyographic measuring apparatus and/or pressure transducer probe of pressure measuring apparatus into the vaginal or anal passage of a person and measuring with the electromyographic or pressure measuring apparatus the appropriate muscle strength of the person while the person is tensing the appropriate muscles in a urine or feces stopping manner to obtain an EMG or pressure signal. The threshold value of a portable electromyographic or pressure measuring unit is then adjusted to enable the person to repeat the measurement at different times to attempt to obtain better EMG or pressure signals in an urge, incontinence or spasm reducing sense. The portable unit gives an audible and/or visual and/or tactile indication when an EMG or pressure signal representing an improvement relative to the threshold value is achieved.

15 Claims, No Drawings

METHOD OF VARYING APPROPRIATE MUSCLE STRENGTH OF A PERSON TO ALLEVIATE URINARY OR FECAL URGENCY OR INCONTINENCE OR VAGINAL OR BLADDER SPASMS

This application is a continuation-in-part of application Ser. No. 08/003,052, filed Jan. 11, 1993, now U.S. Pat. No. 5,291,902.

This invention relates to the treatment of urinary or fecal urgency or incontinence or vaginal or bladder spasms.

Such medical problems are well known and many attempts have been made to provide methods of treatment. However, none of the methods previously proposed have proved to be as successful as desired.

It is therefore an object to the invention to provide an improved method for treating such problems.

According to the invention, a method of varying the appropriate muscle strength of a person to at least alleviate urinary or fecal urgency or incontinence or vaginal or bladder spasms comprises placing a surface electrode of electromyographic measuring apparatus at an appropriate position on the person and/or inserting a probe electrode of electromyographic measuring apparatus and/or a pressure transducer probe of pressure measuring apparatus into the vaginal or anal passage of a person, measuring with said electromyographic or pressure measuring apparatus the appropriate muscle strength of the person while the person is tensing the appropriate muscles in a urine or feces stopping manner to obtain an EMG or pressure signal, and adjusting the threshold value of a portable electromyographic or pressure measuring unit to enable the person to repeat said measurement at different times to attempt to obtain better EMG or pressure signals in an urge, incontinence or spasm reducing sense, said portable unit giving an audible and/or visual and/or tactile indication when an EMG or pressure signal representing an improvement relative to said threshold value is achieved.

When the measurement has been made and the threshold value of the electromyographical or pressure measuring unit has been appropriately adjusted by a professional, the person can perform specified physical exercises which are designed to improve muscle control in a manner to at least alleviate the problem and then use the electromyographic or pressure measuring unit provided to see if better EMG or pressure signals can be obtained, i.e. to see if the exercises are having a beneficial effect. In due course the person will again be checked by a professional and a further measurement made. The professional will then re-adjust the threshold value of the electromyographic or pressure measuring unit to give the person a further incentive to continue the specified physical exercises.

The appropriate muscle strength may be measured while the person is at rest and not consciously tensing the muscles in a urine or feces stopping manner to obtain a first EMG or pressure signal, while the person is tensing the muscles in a urine or feces stopping manner for a short period of time to obtain a second EMG or pressure signal, and while the person is tensing the muscles in a urine or feces stopping manner for a longer period of time to obtain a third EMG or pressure signal. The first signal gives an indication of the person's resting values, the second signal gives an indication of the person's best or highest muscle contraction, and the third signal gives an indication of the fatigue rate of the muscles over time, i.e. as the muscles tire, the values decrease.

The threshold value of the portable electromyographic or pressure unit may be adjusted to a value which is from about 50 to about 90% of the best measurement while the person is tensing the muscles in a urine or feces stopping manner.

The electrodes or probes may be simply applied to the surface of the body or inserted in a body orifice, without implantation being necessary. In other words, the electrodes or probes can be non-invasive. The skin need not be prepared with solvents or broken with needles.

The short period of time may be in the range of from about 2 to about 5 seconds, for example about 2 seconds. The longer period of time may be in the range of from about 10 to about 30 seconds, for example about 10 seconds.

The method may further include applying neuromuscular stimulation in the form of repeated applications of electrical pulses to the pelvic floor muscles to cause the muscles to repeatedly contract and relax and consequently grow and increase in strength to lessen urinary or fecal urgency or incontinence.

The electrical pulses may have a peak current in the range of from about 10 to about 100 milliamps and a frequency in the range of from about 10 about 60 Hz and may be applied in pulses of from about 2 to about 10 seconds with an interval between pulses in the range of from about 4 to about 20 seconds. The interval between pulses is preferably about twice as long as each pulse.

When stress incontinence is to be treated, the electrical pulses may have a peak current in the range of from about 10 to about 100 milliamps and a frequency in the range of from about 40 to about 60 Hertz and be applied in pulses lasting from about 5 to about 10 seconds with an interval between pulses in the range of from about 5 to about 10 seconds.

The electrical pulses may have a peak current of about 40 milliamps and a frequency of about 50 Hz and be applied as pulses lasting from about 5 seconds with an interval between pulses of from about 5 to about 10 seconds.

When urge incontinence is to be treated, the electrical pulses may have a peak current in the range of from about 10 to about 100 milliamps and a frequency in the range of from about 10 to about 15 Hz and be applied as pulses lasting from about 5 to about 10 seconds with an interval between pulses of from about 5 to about 10 seconds.

The electrical pulses may have a peak current of about 40 milliamps and a frequency of about 13 Hz and be applied as pulses lasting for about 5 seconds with an interval between pulses of from about 5 to about 10 seconds.

Urinary incontinence is the inability to control the passage of urine due to weakness of the sphincter and/or pelvic floor muscles. Urinary urgency is the sensation of needing to urinate immediately.

When treating a person with urinary urgency or incontinence in accordance with the invention, the initial treatment session involves the taking of baseline electromyographic and/or pressure measurements of the strength of the muscles of the sphincter and/or pelvic floor which control urination. Suitable equipment for this purpose is, for EMG measurements, the Speakeasy MC (R) equipment which is primarily intended for use in Speech therapy. For pressure measurements, an inflatable pessary with an appropriate pressure gauge, a perionemeter or an appropriate syphgmomanometer can be used. Measurements are made while the person is at rest, while the person is exerting maximum muscle contraction in a urine stopping manner for a short period of time, and while the person is exerting maximum muscle contraction in a urine stopping manner for a longer period of time. For example, the short period of time may be about 2 seconds and the longer period of time may be about 10 seconds.

The person is then taught appropriate exercise such as those known to a person skilled in the art or other suitable exercises to strengthen the appropriate muscles, with emphasis on the short hold time and the longer hold time mentioned above. The person is then given a portable electromyographic feedback or pressure measuring unit for his/her personal use so that the person can practice the exercises at home or elsewhere and seek to improve on the baseline measurements. Suitable equipment for this purpose is, for EMG measurements, the Speakeasy TH (R) equipment which again is primarily intended for use in speech therapy and for pressure measurements, the equipment previously mentioned.

Before giving the unit to the person, the threshold value of the unit is adjusted by a professional to a value related to the person's baseline measurements, for example from about 60 to about 90% of the person's best effort during long hold. The settings for such a unit are typically from about 1 to about 10 microvolts. Thus, the person receives audio and/or visual and/or tactile feedback from the unit and is thereby encouraged to increase the feedback output by producing stronger contractions. The tactile feedback may be a vibration felt by the person, the intensity of the vibration increasing as muscle strength increased.

In addition to the biofeedback exercises, the person is put on a voiding, i.e. bladder emptying, regimen which is regularly adjusted by the professional, for example on a weekly basis. An appropriately set timer may be provided for this purpose. Every time the timer alarm sounds, the person must go to the toilet and try to void.

The person may also be given neuromuscular stimulation in the form of repeated applications of electrical pulses to the appropriate pelvic floor muscles to cause them to repeatedly contract and relax. Suitable equipment for this purpose is the Respond Select equipment manufactured by Medtronic Nortech and intended for use in rebuilding muscles of the shoulder, knee, hip and hand following disease, surgery or injury. Such stimulation causes muscle growth and increased muscle strength and may be applied by surface, rectal or vaginal probe electrodes to the pelvic floor muscles and/or sphincter.

For stress incontinence, namely incontinence caused by various forms of physical activity, the pulses may have a frequency in the range of form about 40 to about 60 Hz, preferably about 50 Hz, and last for about 5 seconds with an off interval of about 10 seconds, increasing to lasting for about 5 seconds with an off interval of about 5 seconds, the session lasting from about 15 to about 30 minutes. There may be several such sessions per day.

It has been found that a frequency of about 50 Hz is preferable for stress incontinence in that it has been found to be the best frequency to enhance the pelvic floor musculature and improve urethral closure without rapid muscle fatigue. In other words, such a frequency automates pelvic floor muscle exercises. It has been found that muscle contraction occurs at or above about 40 Hz and that frequencies somewhat above about 50 Hz cause muscle fatigue. Accordingly therefore, about 50 Hz is the preferred neuromuscular stimulation frequency for treating stress incontinence.

For urge incontinence, namely incontinence caused by a full or nearly full bladder, pulse frequency may be from about 10 to about 15 Hz, preferably about 13 Hz, with the pulses being applied as for stress incontinence.

Urge incontinence is treated with a lower frequency because it has been found that bladder inhibition occurs with lower frequencies. However, at frequencies below about 10 Hz, some people experience discomfort or pain. Accordingly therefore, it has been found that a frequency of from about 13 to about 15 Hz is preferable for treating urge incontinence in that this produces pain-free, low frequency stimulation which results in bladder inhibition by reflexive mechanisms.

It should be pointed out that the intensity of the neuromuscular stimulation is not an exact science but depends on the individual person's reaction to stimuli. The intensity must be sufficient to cause muscle contraction. It has been found that an intensity of about 40 milliamps is usually appropriate for stress incontinence and urge incontinence, but this may not be true in every case. The intensity may in fact be varied in the range of from about 10 to about 100 milliamps.

Specific examples of treatment will now be given. The first example is of a person with urge incontinence and the second example is of a person with stress incontinence. In each example, EMG readings and other information are given for an initial session and for subsequent sessions which occurred at weekly intervals. In Example 1 and Example 2, the EMG signal readings are taken when the person is sitting and when the person is standing, and each reading is taken twice to avoid errors caused by spurious readings. Example 5, 3 to 5 show averaged readings taken from samples over an appropriate period of times while the person is sitting and while the person is standing.

| | EXAMPLE 1 (Urge Incontinence) | | |
|---|---|---|---|
| | | EMG SIGNAL (uV) | |
| | | Sitting | Standing |
| | FIRST SESSION | | |
| 1. | Person at rest | | |
| | Pelvic floor | 1.11/1.20 | 1.3/1.31 |
| | Abdomen | 2.0/2.11 | 1.9/2.20 |
| 2. | Short Hold (2 sec.) | | |
| | Pelvic floor | 2.30/1.9 | 2.21/2.16 |
| | Abdomen | 5.7/5.0 | 6.11/6.01 |
| 3. | Long Hold (10 sec.) | | |
| | Pelvic floor | 1.96/1.90 | 2.01/2.70 |
| | Abdomen | 4.33/4.71 | 5.31/5.44 |
| 4. | Suggested voiding interval | 20 mins | |
| 5. | EMG Home Unit Setting | 1.5 uV. | |
| 6. | Neurostimulation Unit Setting | N/A | |
| 7. | Number of accidents per day | More than 2 | |
| | SECOND SESSION | | |
| 1. | Person at rest | | |
| | Pelvic floor | .97/1.09 | 1.19/1.17 |
| | Abdomen | 1.35/1.01 | 2.00/2.10 |
| 2. | Short Hold (2 sec.) | | |
| | Pelvic floor | 3.96/2.91 | 3.01/3.20 |
| | Abdomen | 1.55/1.73 | 1.96/1.80 |
| 3. | Long Hold (10 sec.) | | |
| | Pelvic floor | 3.44/3.10 | 3.27/3.49 |
| | Abdomen | 1.40/1.75 | 1.90/1.91 |

EXAMPLE 1 (Urge Incontinence) -continued

| | | EMG SIGNAL (uV) | |
|---|---|---|---|
| | | Sitting | Standing |
| 4. | Suggested voiding interval | 45 mins | |
| 5. | EMG Home Unit Setting | 2.4 uV. | |
| 6. | Neurostimulation Unit Setting | N/A | |
| 7. | Number of accidents per day | 1 | |
| THIRD SESSION | | | |
| 1. | Person at rest | | |
| | Pelvic floor | .88/.98 | 1.12/1.20 |
| | Abdomen | N/A | |
| 2. | Short Hold (2 sec.) | | |
| | Pelvic floor | 4.14/4.33 | 4.56/4.9 |
| | Abdomen | N/A | |
| 3/ | Long Hold (10 sec.) | | |
| | Pelvic Floor | 4.01/4.09 | 4.0/3.97 |
| | Abdomen | N/A | |
| 4. | Suggested voiding interval | 60 mins | |
| 5. | EMG Home Unit Setting | 3 uV. | |
| 6. | Neurostimulation Unit Setting | N/A | |
| 7. | Number of accidents per day | 1 | |
| FOURTH SESSION | | | |
| 1. | Person at rest | | |
| | Pelvic floor | .80/.87 | 1.0/.93 |
| | Abdomen | N/A | |
| 2. | Short Hold (2 sec.) | | |
| | Pelvic floor | 6.11/5.87 | 5.9/6.02 |
| | Abdomen | N/A | |
| 3. | Long Hold (10 sec.) | | |
| | Pelvic Floor | 5.44/5.9 | 4.9/5.22 |
| | Abdomen | N/A | |
| 4. | Suggested voiding interval | 90 mins | |
| 5. | EMG Home Unit Setting | 4.1 uV. | |
| 6. | Neurostimulation Unit Setting | N/A | |
| 7. | Number of accidents per day | 0 | |
| FIFTH SESSION | | | |
| 1. | Person at rest | | |
| | Pelvic floor | .81/.89 | 1.02/.95 |
| | Abdomen | N/A | |
| 2. | Short Hold (2 sec.) | | |
| | Pelvic floor | 1.04/9.77 | 10.6/11.01 |
| | Abdomen | N/A | |
| 3. | Long Hold (10 sec.) | | |
| | Pelvic Floor | 9.87/9.8 | 9.9/10.12 |
| | Abdomen | N/A | |
| 4. | Suggested voiding interval | 120 mins | |
| 5. | EMG Home Unit Setting | N/A | |
| 6. | Neurostimulation Unit Setting | N/A | |
| 7. | Number of accidents per day | 0 | |

Comments on Example 1 (Urge Incontinence)

The dramatic improvement by the fifth session is readily apparent. In this example, it was also necessary to measure abdominal muscle activity and to condition the person to lesson such muscle contraction when contracting the pelvic floor muscles. No. neuromuscular stimulation was required.

EXAMPLE 2 (Stress Incontinence)

| | | EMG SIGNAL (uV) | |
|---|---|---|---|
| | | Sitting | Standing |
| FIRST SESSION | | | |
| 1. | Person at rest | | |
| | Pelvic floor | .89/1.07 | .99/1.21 |
| | Abdomen | N/A | |
| 2. | Short Hold (2 sec.) | | |
| | Pelvic floor | 2.11/1.80 | 2.67/2.57 |
| | Abdomen | N/A | |
| 3. | Long Hold (10 sec.) | | |
| | Pelvic Floor | 1.88/1.57 | 2.01/1.98 |
| | Abdomen | N/A | |

EXAMPLE 2 (Stress Incontinence) -continued

| | | EMG SIGNAL (uV) | |
|---|---|---|---|
| | | Sitting | Standing |
| 4. | Suggested voiding interval | 30 mins | |
| 5. | EMG Home Unit Setting | 1.2 uV. | |
| 6. | Neurostimulation Unit Setting | 40 mA | |
| 7. | Number of accidents per day | more than 2 | |
| SECOND SESSION | | | |
| 1. | Person at rest | | |
| | Pelvic floor | .99/.89 | 1.02/1.11 |
| | Abdomen | N/A | |
| 2. | Short Hold (2 sec.) | | |
| | Pelvic floor | 2.99/3.01 | 3.54/3.77 |
| | Abdomen | N/A | |
| 3. | Long Hold (10 sec.) | | |
| | Pelvic Floor | 2.50/2.93 | 3.60/3.89 |
| | Abdomen | N/A | |
| 4. | Suggested voiding interval | 45 mins | |
| 5. | EMG Home Unit Setting | 2.25 uV. | |
| 6. | Neurostimulation Unit Setting | 40 mA | |
| 7. | Number of accidents per day | 3 | |
| THIRD SESSION | | | |
| 1. | Person at rest | | |
| | Pelvic floor | .91/.90 | .99/1.04 |
| | Abdomen | N/A | |
| 2. | Short Hold (2 sec.) | | |
| | Pelvic floor | 3.03/4.11 | 4.01/3.90 |
| | Abdomen | N/A | |
| 3. | Long Hold (10 sec.) | | |
| | Pelvic floor | 3.27/3.98 | 4.21/4.01 |
| | Abdomen | N/A | |
| 4. | Suggested voiding interval | 60 mins | |
| 5. | EMG Home Unit Setting | 3 uV. | |
| 6. | Neurostimulation Unit Setting | Discontinued | |
| 7. | Number of accidents per day | 1 | |
| FOURTH SESSION | | | |
| 1. | Person at rest | | |
| | Pelvic floor | .77/1.01 | .99/1.11 |
| | Abdomen | N/A | |
| 2. | Short Hold (2 sec.) | | |
| | Pelvic floor | 5.11/5.78 | 6.02/6.11 |
| | Abdomen | N/A | |
| 3. | Long Hold (10 sec.) | | |
| | Pelvic floor | 4.97/5.0 | 5.1/5.5 |
| | Abdomen | N/A | |
| 4. | Suggested voiding interval | 90 mins | |
| 5. | EMG Home Unit Setting | 4.5 uV. | |
| 6. | Neurostimulation Unit Setting | N/A | |
| 7. | Number of accidents per day | 0 | |
| FIFTH SESSION | | | |
| 1. | Person at rest | | |
| | Pelvic floor | 1.02/1.09 | 1.20/1.11 |
| | Abdomen | N/A | |
| 2. | Short Hold (2 sec.) | | |
| | Pelvic floor | 8.71/9.21 | 10.11/10.60 |
| | Abdomen | N/A | |
| 3. | Long Hold (10 sec.) | | |
| | Pelvic floor | 8.90/9.01 | 10.02/10.90 |
| | Abdomen | N/A | |
| 4. | Suggested voiding interval | 110 mins | |
| 5. | EMG Home Unit Setting | N/A | |
| 6. | Neurostimulation Unit Setting | N/A | |
| 7. | Number of accidents per day | 0 | |

Comments on Example 2 (Stress Incontinence)

Again the dramatic improvement by the fifth session is readily apparent. In this example, it was not necessary to monitor abdominal muscle activity. However, neuromuscular stimulation was applied.

EXAMPLE 3 (Urinary Incontinence)

| | | EMG uV | PRESSURE |
|---|---|---|---|
| | First Session | | |
| 1. | Person at rest | 1.09 uV surface | |
| | | 1.89 uV vaginal | 11 mmHG vaginal |
| | | 1.45 uV rectal | 9 mmHG rectal |
| 2. | Maximum Contraction | 1.99 uV surface | |
| | | 2.07 uV vaginal | 14 mmHG vaginal |
| | | 2.66 uV rectal | 10 mmHG rectal |
| 3. | Toileting Interval | 30 minutes | |
| 4. | EMG Home Unit Setting | 2.0 uV | |
| 5. | Neuromuscular Stimulation | 1 once per day via a vaginal electrode | |
| 6. | Number of Accidents per Day | 12 | |
| | Second Session | | |
| 1. | Person at rest | 1.00 uV surface | |
| | | 2.01 uV vaginal | 10 mmHG vaginal |
| | | 1.90 uV rectal | 9 mmHG rectal |
| 2. | Maximum Contraction | 3.99 uV surface | |
| | | 4.97 uV vaginal | 16 mmHG vaginal |
| | | 4.66 uV rectal | 16 mmHG rectal |
| 3. | Toileting Interval | 60 minutes | |
| 4. | EMG Home Unit Setting | 3.45 uV | |
| 5. | Neuromuscular Stimulation | once per day | |
| 6. | Number of Accidents per Day | 9 | |
| | Third Session | | |
| 1. | Person at rest | 1.01 uV surface | |
| | | 1.05 uV vaginal | 8 mmHG vaginal |
| | | 1.4 uV rectal | 7 mmHG rectal |
| 2. | Maximum Contraction | 9.99 uV surface | |
| | | 10.07 uV vaginal | 18 mmHG vaginal |
| | | 10.66 uV rectal | 16 mmHG rectal |
| 3. | Toileting Interval | 90 minutes | |
| 4. | EMG Home Unit Setting | 7.3 uV | |
| 5. | Neuromuscular Stimulation | once every other day | |
| 6. | Number of Accidents per Day | 4 | |
| | Fourth Session | | |
| 1. | Person at rest | 1.0 uV surface | |
| | | 1.00 uV vaginal | 6 mmHG vaginal |
| | | 1.04 uV rectal | 5 mmHG rectal |
| 2. | Maximum Contraction | 11.99 uV surface | |
| | | 12.07 uV vaginal | 18 mmHG vaginal |
| | | 10.66 uV rectal | 16 mmHG rectal |
| 3. | Toileting Interval | 150 minutes | |
| 4. | EMG Home Unit Setting | 8.3 uV | |
| 5. | Neuromuscular Stimulation | N/A | |
| 6. | Number of Accidents per Day | 0 | |
| | Fifth Session | | |
| 1. | Person at rest | .9 uV surface | |
| | | 1.02 uV vaginal | 6 mmHG vaginal |
| | | 1.08 uV rectal | 5 mmHG rectal |
| 2. | Maximum Contraction | 12.55 uV surface | |
| | | 13.01 uV vaginal | 19 mmHG vaginal |
| | | 12.78 uV rectal | 18 mmHG rectal |
| 3. | Toileting Interval | 180 minutes | |
| 4. | EMG Home Unit Setting | (discontinued) | |
| 5. | Neuromuscular Stimulation | N/A | |
| 6. | Number of Accidents per Day | 0 | |

Comments on Example 3 (Urinary. Incontinence)

Again, the dramatic improvement is readily apparent. As in Example 2, it was not necessary to monitor abdominal muscle activity but neuromuscular stimulation was applied.

Fecal incontinence is the inability to control the passage of feces due to weakness of the anal sphincter and/or pelvic floor muscles. Fecal urgency is the sensation of needing to defecate immediately.

The procedure for alleviating such problems in accordance with the invention is similar to that for urinary urgency or incontinence, the difference being that the measurements are made while the person is tensing (or not tensing) bowel controlling muscles. An example follows.

EXAMPLE 4 (Fecal Incontinence)

| | | EMG uV | PRESSURE |
|---|---|---|---|
| | First Session | | |
| 1. | Person at rest | 1.09 uV surface | |
| | | 1.89 uV vaginal | 11 mmHG vaginal |
| | | 1.45 uV rectal | 9 mmHG rectal |
| 2. | Maximum Contraction | 1.99 uV surface | |
| | | 2.07 uV vaginal | 14 mmHG vaginal |
| | | 2.66 uV rectal | 10 mmHG rectal |
| 3. | Toileting Interval | 30 minutes | |
| 4. | EMG Home Unit Setting | 2.0 uV | |
| 5. | Neuromuscular Stimulation | N/A | |
| 6. | Number of Accidents per Day | 2 | |
| | Second Session | | |
| 1. | Person at rest | 1.00 uV surface | |
| | | 2.01 uV vaginal | 10 mmHG vaginal |
| | | 1.90 uV rectal | 9 mmHG rectal |
| 2. | Maximum Contraction | 3.99 uV surface | |
| | | 4.07 uV vaginal | 16 mmHG vaginal |
| | | 4.66 rectal | 16 mmHG rectal |
| 3. | Toileting Interval | 60 minutes | |
| 4. | EMG Home Unit Setting | 3.45 uV | |
| 5. | Neuromuscular Stimulation | N/A | |
| 6. | Number of Accidents per Day | 1 | |
| | Third Session | | |
| 1. | Person at rest | 1.01 uV surface | |
| | | 1.05 uV vaginal | 8 mmHG vaginal |
| | | 1.4 uV rectal | 7 mmHG rectal |
| 2. | Maximum Contraction | 9.99 uV surface | |
| | | 10.07 uV vaginal | 18 mmHG vaginal |
| | | 10.66 uV rectal | 16 mmHG rectal |
| 3. | Toileting Interval | 90 minutes | |
| 4. | EMG Home Unit Setting | 7.3 uV | |
| 5. | Neuromuscular Stimulation | N/A | |
| 6. | Number of Accidents per Day | 0 | |

Comments on Example 4 (Fecal Incontinence)

Dramatic improvement is again achieved. No monitoring of abdominal muscle activity or neuromuscular stimulation was necessary in this example.

Vaginismus is painful involuntary spasm of the vagina preventing intercourse. Painful bladder syndrome is characterized by spasms of the bladder.

The procedure for alleviating such problems in accordance with the invention is generally similar to that for urinary or fecal urgency or incontinence. However, for EMG readings, sensors are placed on the perineum anterior to the anus and posterior to the vagina. A period of time is allowed for the patient to relax as the application of the sensors may have initiated vaginal spasm. Also, readings may be taken while the person attempts to relax and a small speculum or probe is introduced into the vagina to elicit spasm. An example follows.

EXAMPLE 5 (Vaginismus)

| | | EMG uV | PRESSURE |
|---|---|---|---|
| | First Session | | |
| 1. | Person at rest | 16.09 uV surface | |
| | | 18.89 uV vaginal | 21 mmHG vaginal |
| | | 19.45 uV rectal | 18 mmHG rectal |
| 2. | Maximum Contraction | 19.99 uV surface | |
| | | 22.07 uV vaginal | 24 mmHG vaginal |
| | | 23.66 uV rectal | 20 mmHG rectal |
| 3. | Toileting Interval | N/A | |
| 4. | EMG Home Unit Setting | 16.0 uV | |
| 5. | Neuromuscular Stimulation | N/A | |
| | Second Session | | |
| 1. | Person at rest | 11.09 uV surface | |
| | | 12.89 uV vaginal | 11 mmHG vaginal |
| | | 12.45 uV rectal | 10 mmHG rectal |
| 2. | Maximum Contraction | 14.99 uV surface | |
| | | 18.07 uV vaginal | 14 mmHG vaginal |
| | | 17.66 uV rectal | 15 mmHG rectal |
| 3. | Toileting Interval | N/A | |
| 4. | EMG Home Unit Setting | 12.0 uV | |
| 5. | Neuromuscular Stimulation | N/A | |
| | Third Session | | |
| 1. | Person at Rest | 6.09 uV surface | |
| | | 8.89 uV vaginal | 11 mmHG vaginal |
| | | 9.45 uV rectal | 11 mmHG rectal |
| 2. | Maximum Contraction | 14.99 uV surface | |
| | | 17.07 uV vaginal | 16. mmHG vaginal |
| | | 18.66 uV rectal | 14 mmHG rectal |
| 3. | Toileting Interval | N/A | |
| 4. | EMG Home Unit Setting | 12 uV | |
| 5. | Neuromuscular Stimulation | N/A | |
| | Fourth Session | | |
| 1. | Person at rest | 2.09 uV surface | |
| | | 3.89 uV vaginal | 8 mmHH vaginal |
| | | 2.0 uV rectal | 8 mmHG rectal |
| 2. | Maximum Contraction | 19 uV surface | |
| | | 19.07 uV vaginal | 24 mmHG vaginal |
| | | 21.66 uV rectal | 20 mmHG rectal |
| 3. | Toileting Interval | N/A | |
| 4. | EMG Home Unit Setting | N/A | |
| 5. | Neuromuscular Stimulation | N/A | |

Comments on Example 5 (Vaginismus).

Dramatic improvement is again achieved. In this example, no monitoring of abdominal muscular activity or neuromuscular stimulation was required.

The above examples demonstrate the advantages of the invention. Other embodiments of the invention will be readily apparent to a person skilled in the art from the foregoing description. For example, it will be appreciated that the invention may also be used to alleviate cystocele, rectocele, or bladder, bowel or vaginal prolapse. The scope of the invention is defined in the appended claims.

I claim:

1. A method of varying the appropriate muscle strength of a person to at least alleviate urinary or fecal urgency or incontinence, or vaginal or bladder spasms comprising:

placing a surface electrode of electromyographic measuring apparatus at an appropriate position on the person and/or inserting a probe electrode of electromyographic measuring apparatus and/or pressure transducer probe of pressure measuring apparatus into the vaginal or anal passage of a person, measuring with said electromyographic or pressure measuring apparatus the appropriate muscle strength of the person while the person is at rest and not consciously tensing the appropriate muscles in a urine or feces stopping manner to obtain a first EMG or pressure signal, while the person is tensing the appropriate muscles in a urine or feces stopping manner for a short period of time to obtain a second EMG or pressure signal, and while the person is tensing the appropriate muscles in a urine or feces stopping manner for a longer period of time to obtain a third EMG or pressure signal, and adjusting the threshold value of a portable electromyographic or pressure measuring unit to enable the person to repeat said measurements at different times to attempt to obtain better EMG or pressure signals in an urge, incontinence or spasm reducing sense, said portable unit giving an audible and/or visual and/or tactile indication when an EMG or pressure signal representing an improvement relative to said threshold value is achieved.

2. A method according to claim 1 wherein the threshold value of the portable electromyographic or pressure measuring unit is adjusted to a value which is from about 50 to about 90% of the best measurement while the person is tensing the appropriate muscles in a urine or feces stopping manner.

3. A method according to claim 1 wherein the short period of time is in the range of from about 2 to about 5 seconds.

4. A method according to claim 3 wherein the short period of time is about 2 seconds.

5. A method according to claim 1 wherein the longer period of time is in the range of from about 10 to about 90 seconds.

6. A method according to claim 5 wherein the longer period of time is about 10 seconds.

7. A method according to claim 1 wherein the short period of time is in the range of from about 2 to about 5 seconds and the longer period of time is in the range of from about 10 to about 90 seconds.

8. A method according to claim 7 wherein the short period of time is about 2 seconds and the longer period of time is about 10 seconds.

9. A method according to claim 1 further including:
repeatedly applying neuromuscular stimulation in the form of electrical pulses to the appropriate muscles to cause the muscles to repeatedly contract and relax and consequently increase in strength to at least alleviate urinary or fecal urgency or incontinence.

10. A method according to claim 9 wherein urinary or fecal incontinence or urgency is to be alleviated and said electrical pulses have a peak current in the range of from about 10 to about 100 milliamps and a frequency in the range of from about 10 to about 60 Hzs. and are applied in pulses lasting from about 2 to about 10 seconds with an interval between pulses in the range of from about 4 to about 20 seconds.

11. A method according to claim 10 wherein the interval between pulses is about twice as long as each pulse.

12. A method according to claim 9 wherein stress incontinence is to be treated and the electric pulses have a peak current in the range of from about 10 to about 100 milliamps and a frequency in the range of from about 40 to about 60 Hz and are applied as pulses lasting from about 5 to about 10 seconds with an interval between pulses in the range of from about 5 to about 10 seconds.

13. A method according to claim 12 wherein said electric impulses have a peak current of about 40 milliamps and a frequency of about 50 Hz and are applied as pulses lasting for about 5 seconds with an interval between pulses in the range of from about 5 to about 10 seconds.

14. A method according to claim 9 wherein urge incontinence is to be treated and said electrical pulses have peak current in the range of from about 10 about 100 milliamps and a frequency in the range of from about 10 to about 15 Hzs. and are applied in pulses lasting from about 5 to about 10 seconds with an interval between pulses in the range of from about 5 to about 20 seconds.

15. A method according to claim 14 wherein said electric impulses have a peak current of about 40 milliamps and a frequency of about 13 Hz and are applied as pulses for about 5 seconds with an interval between pulses in the range of from about 5 to about 10 seconds.

* * * * *